(12) United States Patent
Tischler

(10) Patent No.: US 11,020,123 B2
(45) Date of Patent: Jun. 1, 2021

(54) OCCLUSIVE MEDICAL DEVICE WITH CUSHIONING MEMBER

(71) Applicant: BOSTON SCIENTIFIC SCIMED, INC., Maple Grove, MN (US)

(72) Inventor: Brian Joseph Tischler, Shoreview, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 109 days.

(21) Appl. No.: 16/171,506

(22) Filed: Oct. 26, 2018

(65) Prior Publication Data

US 2019/0125362 A1 May 2, 2019

Related U.S. Application Data

(60) Provisional application No. 62/577,777, filed on Oct. 27, 2017.

(51) Int. Cl.
*A61B 17/12* (2006.01)
*A61B 90/00* (2016.01)
*A61B 17/00* (2006.01)

(52) U.S. Cl.
CPC .. *A61B 17/12122* (2013.01); *A61B 17/12031* (2013.01); *A61B 17/12172* (2013.01); *A61B 17/12177* (2013.01); *A61B 2017/00243* (2013.01); *A61B 2017/00592* (2013.01); *A61B 2017/00601* (2013.01);
(Continued)

(58) Field of Classification Search
CPC ........ A61B 17/12122; A61B 17/12031; A61B 17/12172; A61B 17/12177; A61B 17/00592; A61B 17/00601; A61B 17/00632; A61B 2090/08201; A61B 2017/00243; A61B 2017/08201; A61B 2017/1205; A61F 2/24
See application file for complete search history.

(56) References Cited

U.S. PATENT DOCUMENTS 5,133,733 A 7/1992 Rasmussen et al.
6,214,029 B1 4/2001 Thill et al.
(Continued)

FOREIGN PATENT DOCUMENTS

CN 1278713 A 1/2001
CN 1399571 A 2/2003
(Continued)

OTHER PUBLICATIONS

International Search Report and Written Opinion dated Apr. 22, 2014 for of the International Application No. PCT/US2013/078454.
(Continued)

*Primary Examiner* — Sarah A Simpson
(74) *Attorney, Agent, or Firm* — Seager, Tufte & Wickhem LLP

(57) ABSTRACT

An example occlusive implant is disclosed. The example occlusive implant includes a framework including a projection and a cushioning member coupled to the framework, the cushioning member including a first end region and a second end region opposite the first end region. Additionally, the first end region is coupled to the projection, the second end region is coupled to the framework and the cushioning member includes a curved portion designed to minimize trauma to a target site.

11 Claims, 9 Drawing Sheets

(52) U.S. Cl.
CPC ............... *A61B 2017/00632* (2013.01); *A61B 2017/1205* (2013.01); *A61B 2090/08021* (2016.02)

(56) References Cited

U.S. PATENT DOCUMENTS

| | | | |
|---|---|---|---|
| 6,231,561 B1 | 5/2001 | Frazier et al. | |
| 7,727,189 B2 | 6/2010 | VanTassel et al. | |
| 7,803,171 B1 | 9/2010 | Uflacker | |
| 7,972,359 B2 | 7/2011 | Kreidler | |
| 8,221,384 B2 | 7/2012 | Frazier et al. | |
| 8,562,509 B2 | 10/2013 | Bates | |
| 8,734,480 B2 | 5/2014 | Snow | |
| 9,259,337 B2 * | 2/2016 | Cox | A61F 2/86 |
| 9,913,652 B2 * | 3/2018 | Bridgeman | A61B 17/0057 |
| 2002/0193828 A1 | 12/2002 | Griffin | |
| 2003/0130680 A1 | 7/2003 | Russell | |
| 2003/0208214 A1 | 11/2003 | Loshakove et al. | |
| 2004/0220682 A1 | 11/2004 | Levine et al. | |
| 2005/0125020 A1 | 6/2005 | Meade et al. | |
| 2007/0167975 A1 | 7/2007 | Boyle et al. | |
| 2007/0198050 A1 | 8/2007 | Ravenscroft et al. | |
| 2008/0300620 A1 | 12/2008 | Chanduszko | |
| 2009/0005803 A1 | 1/2009 | Batiste | |
| 2010/0121373 A1 | 5/2010 | Tekulve | |
| 2011/0054515 A1 * | 3/2011 | Bridgeman | A61B 17/0057 606/200 |
| 2012/0065667 A1 | 3/2012 | Javois et al. | |
| 2012/0172654 A1 | 7/2012 | Bates | |
| 2012/0245619 A1 | 9/2012 | Guest et al. | |
| 2012/0316584 A1 | 12/2012 | Miles et al. | |
| 2013/0035713 A1 | 2/2013 | Snow | |
| 2013/0138138 A1 * | 5/2013 | Clark | A61B 17/12177 606/200 |
| 2014/0074151 A1 | 3/2014 | Tischler et al. | |
| 2014/0135817 A1 * | 5/2014 | Tischler | A61B 17/12122 606/200 |
| 2014/0188157 A1 * | 7/2014 | Clark | A61B 17/12122 606/200 |
| 2015/0351904 A1 * | 12/2015 | Cooper | A61F 2/2418 623/2.1 |
| 2016/0278749 A1 | 9/2016 | Javois et al. | |

FOREIGN PATENT DOCUMENTS

| | | |
|---|---|---|
| EP | 0430848 A1 | 6/1991 |
| EP | 1595504 A1 | 11/2005 |
| EP | 2481381 A1 | 8/2012 |
| EP | 3213695 A2 | 9/2017 |
| JP | 2003529384 A | 10/2003 |
| JP | 2003532457 A | 11/2003 |
| JP | 2005503199 A | 2/2005 |
| JP | 2005515830 A | 6/2005 |
| JP | 2005324019 A | 11/2005 |
| JP | 2007513684 A | 5/2007 |
| JP | 2009504365 A | 2/2009 |
| WO | 9923976 A1 | 5/1999 |
| WO | 0027292 A1 | 5/2000 |
| WO | 0035352 A1 | 6/2000 |
| WO | 0121247 A1 | 3/2001 |
| WO | 0170119 A1 | 9/2001 |
| WO | 03032818 A2 | 4/2003 |
| WO | 03063732 A2 | 8/2003 |
| WO | 2007044536 A2 | 4/2007 |
| WO | 2013022567 A2 | 2/2013 |
| WO | 2014106239 A1 | 7/2014 |

OTHER PUBLICATIONS

Cline, "File: Fish hooks.jpg,", Wikipedia Foundation, Inc. p. 1 of 4; Jun. 2007. Available online at http://en.wikipedia.org./wiki/File:Fish_hooks.jpg;last accessed Oct. 5, 2012.
International Search Report and Written Opinion dated Feb. 4, 2019 for International Application No. PCT/US2018/057641.

* cited by examiner

OCCLUSIVE MEDICAL DEVICE WITH CUSHIONING MEMBER

CROSS-REFERENCE TO RELATED APPLICATIONS

This application claims the benefit of priority under 35 U.S.C. § 119 to U.S. Provisional Application Ser. No. 62/577,777, filed Oct. 27, 2017, the entirety of which is incorporated herein by reference.

BACKGROUND

The left atrial appendage (LAA) is a small organ attached to the left atrium of the heart as a pouch-like extension. In patients suffering from atrial fibrillation, the left atrial appendage may not properly contract with the left atrium, causing stagnant blood to pool within its interior, which can lead to the undesirable formation of thrombi within the left atrial appendage. Thrombi forming in the left atrial appendage may break loose from this area and enter the blood stream. Thrombi that migrate through the blood vessels may eventually plug a smaller vessel downstream and thereby contribute to stroke or heart attack. Clinical studies have shown that the majority of blood clots in patients with atrial fibrillation are found in the left atrial appendage. As a treatment, medical devices have been developed which are positioned in the left atrial appendage and deployed to close off the ostium of the left atrial appendage. Over time, the exposed surface(s) spanning the ostium of the left atrial appendage becomes covered with tissue (a process called endothelization), effectively removing the left atrial appendage from the circulatory system and reducing or eliminating the number of thrombi which may enter the blood stream from the left atrial appendage. A continuing need exists for improved medical devices and methods to control thrombus formation within the left atrial appendage of patients suffering from atrial fibrillation.

SUMMARY

An example occlusive implant includes a framework including a projection and a cushioning member coupled to the framework, the cushioning member including a first end region and a second end region opposite the first end region. Additionally, the first end region is coupled to the projection, the second end region is coupled to the framework and the cushioning member includes a curved portion designed to minimize trauma to a target site.

In addition or alternatively, wherein the cushioning member folds back on itself.

In addition or alternatively, wherein the second end region of the cushioning member is attached to an outer surface of the framework.

In addition or alternatively, wherein the second end region of the cushioning member extends through an aperture formed in the framework.

In addition or alternatively, further comprising an occlusive member disposed along at least a portion of the framework.

In addition or alternatively, wherein the occlusive member is attached to the cushioning member.

In addition or alternatively, further comprising an anchor member coupled to the cushioning member.

In addition or alternatively, further comprising a plurality of projections extending circumferentially around a central axis of the expandable framework.

In addition or alternatively, further comprising a plurality of cushioning members, wherein each of the plurality of cushioning members is coupled to a corresponding projection.

In addition or alternatively, wherein the framework is configured to shift between a collapsed configuration and an expanded configuration.

In addition or alternatively, wherein the cushioning member folds inward toward a central axis of the framework.

In addition or alternatively, wherein the cushioning member is configured to translate through the aperture formed in the framework.

Another medical implant for occluding a left atrial appendage, comprising:

an expandable framework including a plurality of projections, wherein the framework is configured to shift between a collapsed configuration and an expanded configuration; and a plurality of cushioning members, wherein each one of the plurality of cushioning members includes a first end coupled to a corresponding projection and a second end coupled to the expandable framework;

wherein the plurality of projections extend circumferentially around a central axis of the expandable framework;

wherein at least one of the plurality of cushioning members includes a curved portion designed to minimize trauma to a target site.

In addition or alternatively, wherein the at least one of the plurality of cushioning members including the curved portion folds back on itself.

In addition or alternatively, the at least one of the plurality of cushioning members including the curved portion folds inward toward a central axis of the framework.

In addition or alternatively, further comprising an occlusive member attached to at least one of the plurality of cushioning members.

In addition or alternatively, wherein the first end region of each of the plurality of cushioning members is attached to an outer surface of the framework.

In addition or alternatively, wherein the first end region of each of the plurality of cushioning members extends through an aperture formed in the framework.

An example method for occluding a left atrial appendage includes:

advancing an occlusive implant to the left atrial appendage, the occlusive implant including:

an expandable framework including a projection; and a cushioning member including a first end region and a second end region opposite the first end region;

wherein the first end region is coupled to the projection;

wherein the second end region is coupled to the framework;

wherein the cushioning member includes a curved portion designed to minimize trauma to a target site;

expanding the framework within the left atrial appendage.

In addition or alternatively, wherein the cushioning member folds back on itself, and wherein the second end region of the cushioning member is attached to an outer surface of the framework.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description of various embodiments in connection with the accompanying drawings, in which.

Figure 1:
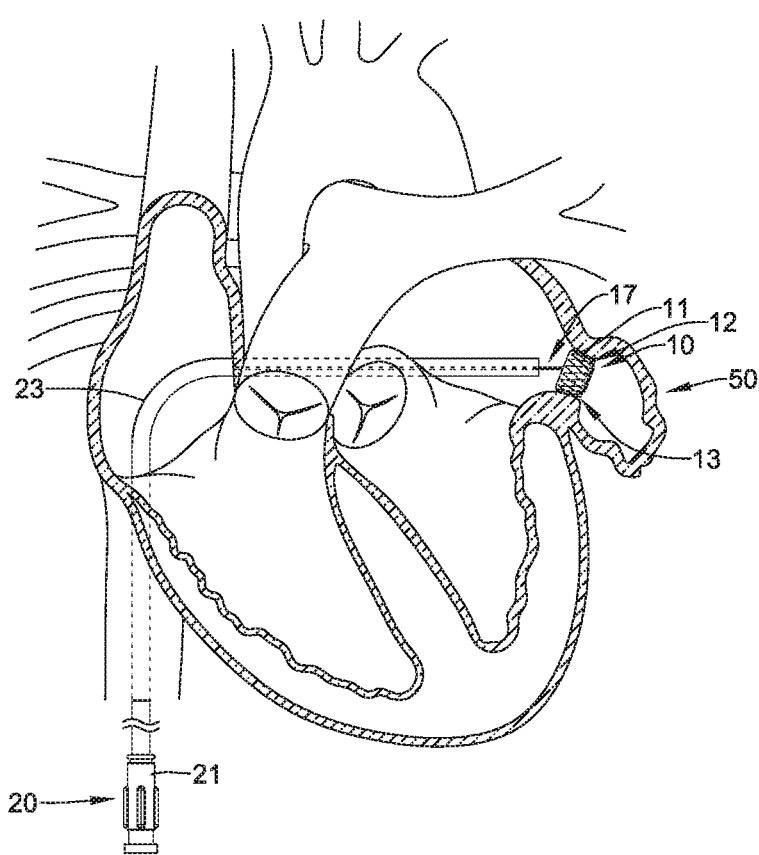
FIG. 1 shows an example occlusive implant positioned in the heart.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed disclosure. Those skilled in the art will recognize that the various elements described and/or shown may be arranged in various combinations and configurations without departing from the scope of the disclosure. The detailed description and drawings illustrate example embodiments of the claimed disclosure. However, in the interest of clarity and ease of understanding, while every feature and/or element may not be shown in each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosure are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device.

The term "extent" may be understood to mean a greatest measurement of a stated or identified dimension, unless the extent or dimension in question is preceded by or identified as a "minimum", which may be understood to mean a smallest measurement of the stated or identified dimension. For example, "outer extent" may be understood to mean a maximum outer dimension, "radial extent" may be understood to mean a maximum radial dimension, "longitudinal extent" may be understood to mean a maximum longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage, while a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

The occurrence of thrombi in the left atrial appendage (LAA) during atrial fibrillation may be due to stagnancy of blood pooling in the LAA. The pooled blood may still be pulled out of the left atrium by the left ventricle, however less effectively due to the irregular contraction of the left atrium caused by atrial fibrillation. Therefore, instead of an active support of the blood flow by a contracting left atrium and left atrial appendage, filling of the left ventricle may depend primarily or solely on the suction effect created by the left ventricle. However, the contraction of the left atrial appendage may not be in sync with the cycle of the left ventricle. For example, contraction of the left atrial appendage may be out of phase up to 180 degrees with the left ventricle, which may create significant resistance to the desired flow of blood. Further still, most left atrial appendage geometries are complex and highly variable, with large irregular surface areas and a narrow ostium or opening compared to the depth of the left atrial appendage. These aspects as well as others, taken individually or in various combinations, may lead to high flow resistance of blood out of the left atrial appendage.

In an effort to reduce the occurrence of thrombi formation within the left atrial appendage and prevent thrombi from entering the blood stream from within the left atrial appendage, it may be desirable to develop medical devices and/or occlusive implants that close off the left atrial appendage from the heart and/or circulatory system, thereby lowering the risk of stroke due to thrombolytic material entering the blood stream from the left atrial appendage. Example medical devices and/or occlusive implants that close off the left atrial appendage are disclosed herein.

FIG. 1 illustrates an occlusive implant 10 which has been inserted and advanced through a body lumen via an occlusive implant delivery system. FIG. 1 further illustrates the occlusive implant 10 being delivered and positioned within the left atrial appendage 50. As will be described in greater detail below, the occlusive implant may include an expandable framework 12 which includes a proximal end region 11 and a distal end region 13 In some instances, an occlusive implant delivery system may include a delivery catheter 23 which is guided toward the left atrium via various chambers and lumens of the heart (e.g., the inferior vena cava, the right atrium, etc.) to a position adjacent the left atrial appendage 50.

The delivery catheter 23 may include a hub member 21. The hub member 21 may be manipulated by a clinician to direct the distal end region of the delivery catheter 23 to a position adjacent the left atrial appendage 50. In some embodiments, an occlusive implant delivery system may include a core wire 17. Further, a proximal end 11 of the expandable framework 12 may be configured to releasably attach, join, couple, engage, or otherwise connect to the distal end of the core wire 17. In some embodiments, the proximal end region 11 of the expandable framework 12 may include a threaded insert coupled thereto. In some embodiments, the threaded insert may be configured to and/or adapted to couple with, join to, mate with, or otherwise engage a threaded member disposed at the distal end of a core wire 17. Other means of releasably coupling and/or engaging the proximal end of the expandable framework 12 to the distal end of the core wire 17 are also contemplated.

FIG. 1 further illustrates the occlusive implant 10 positioned adjacent the left atrial appendage 50 via the delivery catheter 23 (described above). It can be appreciated that in some examples, the implant 10 may be configured to shift between a collapsed configuration and an expanded configuration. For example, in some instances, the occlusive implant 10 may be in a collapsed configuration during delivery via occlusion implant delivery system, whereby the occlusive implant 10 expands to an expanded configuration once deployed from the occlusion implant delivery system.

Additionally, FIG. 1 illustrates that the expandable framework 12 may be compliant and, therefore, substantially conform to and/or be in sealing engagement with the shape and/or geometry of a lateral wall of a left atrial appendage 50 in the expanded configuration. In some embodiments, the occlusive implant 10 may expand to a size, extent, or shape less than or different from a maximum unconstrained extent, as determined by the surrounding tissue and/or lateral wall of the left atrial appendage 50.

Further, it can be appreciated that the elements of the expandable framework 12 may be tailored to increase the flexibility of the expandable framework 12 and/or the occlusive implant 10, thereby permitting the expandable framework 12 and/or the occlusive implant 10 to conform to the tissue around it, rather than forcing the tissue to conform to the expandable framework 12 and/or the occlusive implant 10. Additionally, in some instances, it may be desirable to design the occlusive implant 10 discussed above to include various features, components and/or configurations which improve the sealing capabilities of the occlusive implant within the left atrial appendage.

For example, FIG. 1 illustrates that the distal end region 13 of the expandable framework 12 may extend farther into the left atrial appendage 50 as compared to the proximal end region 11 of the expandable framework 12. It can be appreciated that as the expandable framework is advanced into the left atrial appendage 50, the distal end region 13 may engage with tissue defining the left atrial appendage 50. In other words, the distal end region 13 may be considered the "leading" region of the expandable framework 12 as it enters into the left atrial appendage 50. Therefore, it can further be appreciated that it may be desirable to design the distal end region 13 of the expandable framework to the include features which provide an atraumatic engagement with the heart tissue defining the left atrial appendage 50. Examples of occlusive implants including features designed to provide atraumatic engagement with the heart tissue are described below.

Figure 2:
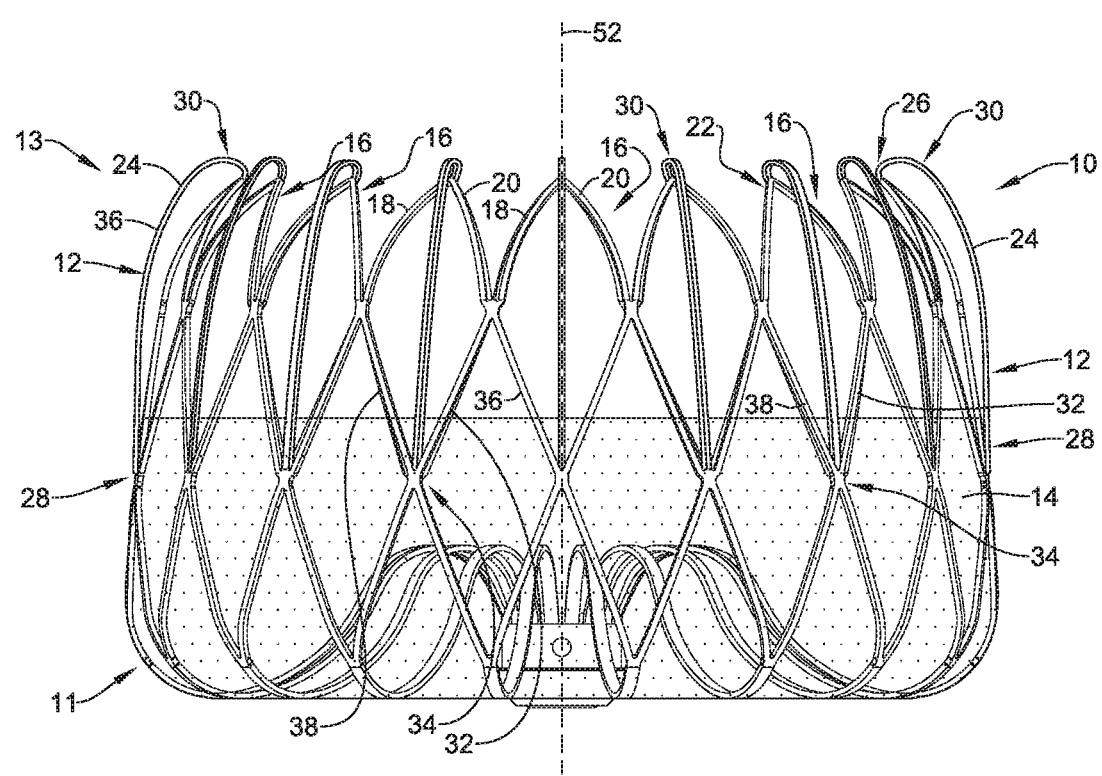
FIG. 2 is a plan view of an example occlusive implant.

FIG. 2 illustrates an example occlusive implant 10. The implant 10 may include an expandable framework 12. The occlusive implant 10 may also include an occlusive member 14 disposed on, disposed over, disposed about, or covering at least a portion of the expandable framework 12. In some embodiments, the occlusive member 14 may be disposed on, disposed over, disposed about or cover at least a portion of an outer (or outwardly-facing) surface of the expandable framework 12. FIG. 1 further illustrates that the occlusive member 14 may extend only partially along the longitudinal extent of the expandable framework 12. However, this is not intended to be limiting. Rather, the occlusive member 14 may extend along the longitudinal extent of the expandable framework to any degree (e.g., the full longitudinal extend of the expandable framework 12).

In some embodiments, the occlusive member 14 may be permeable or impermeable to blood and/or other fluids, such as water. In some embodiments, the occlusive member 14 may include a woven, braided and/or knitted material, a fiber, a sheet-like material, a polymeric membrane, a metallic or polymeric mesh, a porous filter-like material, or other suitable construction. In some embodiments, the occlusive member 14 may prevent thrombi (i.e. blood clots, etc.) from passing through the occlusive member 14 and out of the left atrial appendage into the blood stream. In some embodiments, the occlusive member 14 may promote endothelization after implantation, thereby effectively removing the left atrial appendage from the patient's circulatory system. Some suitable, but non-limiting, examples of materials for the occlusive member 14 are discussed below.

As described above with respect to FIG. 1, the expandable framework 12 may include a proximal end region 11 and a distal end region 13. FIG. 2 further illustrates that the expandable framework 12 may include one or more projections 16 extending in a proximal-to-distal direction. Each of the projections 16 may include a first support member 18 and a second support member 20. As illustrated in FIG. 2, the first support member 18 and the second support member 20 (of each projection 16) may extend in a proximal-to-distal direction and connect with one another at an apex 22. In some instances (such as that shown in FIG. 2), plurality of projections 16 may extend circumferentially around a central axis 52 of the expandable framework 12. In other words, in some examples the projections 16 may resemble the peaks of a "crown" extending circumferentially around a central axis 52 of the expandable framework 12.

FIG. 2 further illustrates that the expandable framework 12 may include one or more cushioning members 24. Each cushioning member 24 may include a first end region 26 and a second end region 28 opposite the first end region 26. As shown in FIG. 2, in at least some examples the first end region 26 of each of the cushioning members 24 may be attached to a corresponding apex 22 of each corresponding projection 16.

Additionally, FIG. 2 illustrates that in some examples, one or more cushioning members 24 may fold back on themselves (e.g., invert on themselves) and attach to the outer surface 36 of the expandable framework 12. FIG. 2 illustrates that the second end region 28 of each of the cushioning member 24 may be attached at an intersection 34 of a first framework member 32 and a second framework member 38. It can be appreciated that a plurality of intersections 34 may be formed throughout the framework 12 via several first framework members 32 connecting with corresponding second framework members 38. Further, it can be appreciated that in some examples, a single cushioning member 24 may attach itself at a single intersection 34 along the framework 12. However, it is also contemplated that in some examples, two or more cushioning members 24 may attach themselves at a single intersection 34 along the framework 12.

Additionally, FIG. 2 illustrates that by folding back on itself, the cushioning members 24 may include a general curved portion 30 extending along their length. As illustrated in FIG. 2, a region of the curved portion 30 may extend distally beyond the apex 22 of each projection 16. This is important because it permits the curved portions 30 of each of the cushioning members 24 to contact the heart tissue as the expandable framework 12 is positioned (e.g., advanced into) the left atrial appendage. Further, it can be appreciated that the curved portion 30 may create a softer, atraumatic surface for engagement with the heart tissue. In other words, the curved portion 30 of each of the cushioning members 24 may create a surface geometry which does not pierce, bite into, dig into, tear, cut, scrape, etc. the heart tissue for which the occlusion member may engage when being positioned within the left atrial appendage. Rather, the curved portions 30 may flex and slide along the tissue defining the left atrial appendage, while continuing to maintain sufficient radial force to sufficiently position the occlusive implant within the opening of the left atrial appendage.

While the above discussion (and the illustration shown in FIG. 2), shows a plurality of projections 16 and cushioning members 24, it is contemplated that the occlusive implant 10 may include 1, 2, 3, 4, 5, 6, 7, 8, 9, 10, 11, 12 or more individual projections 16 and corresponding cushioning members 24 disposed in a variety of arrangements along the expandable framework 12.

Figure 3:
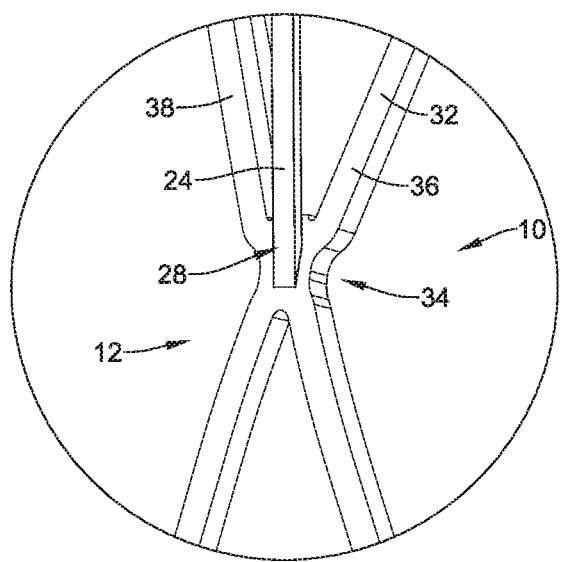
FIG. 3 illustrates an example occlusive implant.

FIG. 3 illustrates a detailed view of an example cushioning member 24 attached to the outer surface 36 of the expandable framework 12. As discussed above, the cushioning member 24 may include a second end region 28 that is attached to the expandable framework 12 at an intersection 34. As illustrated in the detailed view of FIG. 3, the intersection 34 may be described as an area along the framework 12 where a first framework member 32 joins a second framework member 38. It can be appreciated that the second end region 28 of the cushioning member 24 may be attached to the outer surface 36 of the expandable framework 12 through a variety of attachment techniques. For example, the second end region 28 of the cushioning member 24 may be attached to the outer surface 36 of the expandable framework via welding, press fit, mechanical snap fit, keyed mechanical lock, etc.

Figure 4:
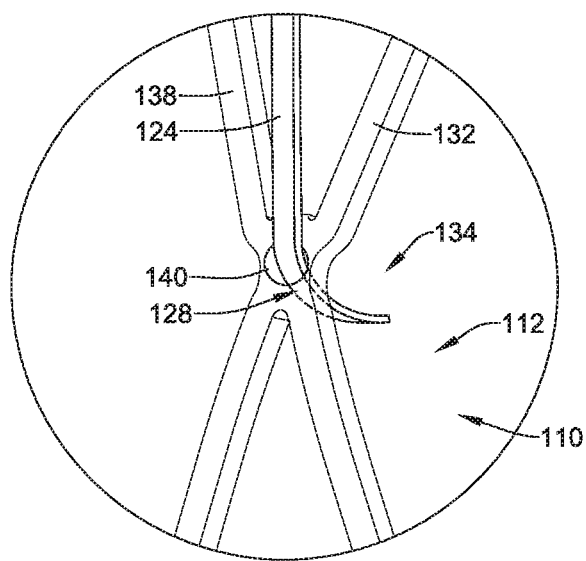
FIG. 4 illustrates another example occlusive implant.

FIG. 4 illustrates a detailed view of an alternative attachment technique for attaching an example cushioning member 124 to an expandable framework 112 of an example occlusion device 110. The example framework 112 shown in FIG. 4 may be similar in form and function to the expandable framework 12 shown in FIG. 3. For example, the framework 112 may include a cushioning member 124 having a second end region 128. Further, the expandable framework 112 may include an intersection 134 where a first supporting member 132 joins a second supporting member 138. However, it can be further appreciated that the second end region 128 of the cushioning member 124 may be attached to the expandable framework 112 by extending through an aperture 140 formed in the expandable framework 112. For example, the second end region 128 of the cushioning member 124 may be attached to the outer surface 136 of the expandable framework by being press fit through an aperture 140 sized to form a secure engagement with the second end region 128 of the cushioning member 124. Additionally, it is contemplated that the second end region 128 of the cushioning member may be rigidly fixed within the aperture 140 via a variety of securement methods (e.g., welding, gluing, etc.) For example, the second end region 128 of the cushioning member 124 may include a weld ball (not shown) which is designed to prevent the second end region 128 from being pulled back through the aperture 140.

While the above discussion illustrates one example in which the cushioning member 124 is attached to the outer surface 136 of the expandable framework 112, other securement techniques are contemplated. For example, it is contemplated that the cushioning member 124 shown in FIG. 4 need not be attached to the outer surface 136 of the expandable framework 112. For example, it is contemplated that the second end region 128 of the cushioning member 124 may "slide" or translate through the aperture 140. It can be appreciated that the length of the second end region 128 of the cushioning member 124 may be designed to prevent the second end region 128 from passing back through the aperture 140. Allowing the second end region 128 to slide and/or translate through the aperture 140 may permit the second end region 128 to shift, pivot and/or rotate (e.g., change its angle) as it is constrained and pulled into a catheter, for example. For example, allowing the second end region 128 to slide and/or translate through the aperture 140 may provide the cushioning members 124 an additional degree of freedom with which to move as the occlusion device 110 interacts with a delivery catheter during delivery and/or recapture of the occlusion device 110.

Figure 5:
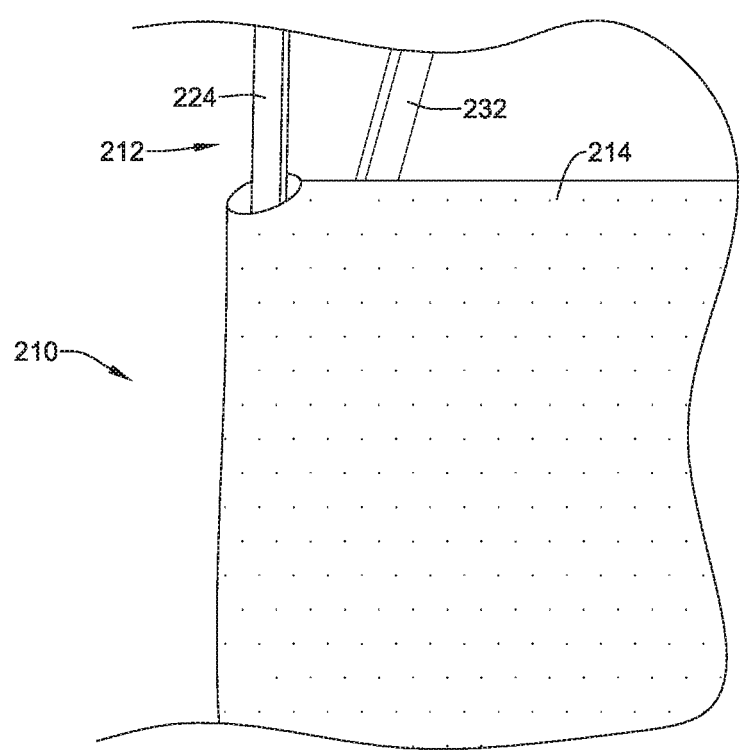
FIG. 5 illustrates another example occlusive implant.

FIG. 5 illustrates a detailed view of another example occlusion implant device 210. The occlusion implant device 210 may be similar in form and function to other occlusion implant devices disclosed herein. For example, the occlusion implant device 210 may include an expandable frame 212 including a cushioning member 224 and a first supporting member 232. Further, FIG. 5 illustrates that the occlusion implant device 210 may include an occlusion member 214. FIG. 5 further illustrates that in some examples the occlusion member 214 may be attached to the expandable frame 212 by being attached to the cushioning member 224. For example, FIG. 5 illustrates that, in some examples, the occlusion member 214 may be attached to the expandable framework 212 by looping a portion of the occlusion member 214 around one or more of the cushioning members 224. Other attachment techniques are contemplated. For example, it is contemplated that the occlusion member 214 may be attached to the expandable framework 212 by securing (e.g., pinching) the occlusion member 214 between the cushioning member 224 and a portion of the expandable framework 212 (e.g., the first supporting member 232).

Figure 6:
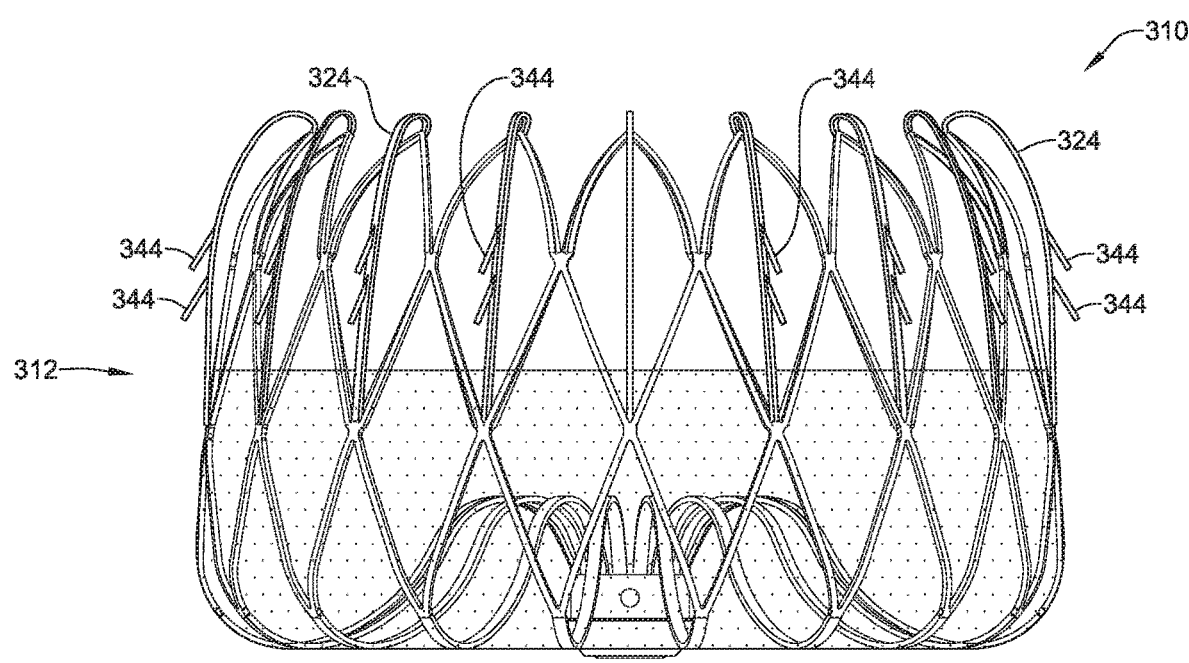
FIG. 6 illustrates another example occlusive implant.

FIG. 6 illustrates a detailed view of another example occlusion implant device 310. The occlusion implant device 310 may be similar in form and function to other occlusion implant devices disclosed herein. For example, the occlusion implant device 310 may include an expandable frame 312 including one or more cushioning members 324. Additionally, FIG. 6 illustrates that the occlusion device 310 may include a plurality of anchor members 344 disposed along the cushioning members 324. It is contemplated that any of the example occlusive devices described herein may include one or more anchoring members 344 described with respect to FIG. 6. Further, it can be appreciated that the expandable framework 312 may be held fixed adjacent to the left atrial appendage by one or more anchoring members 344. The plurality of anchor members 344 may extend radially outward from the expandable framework 312. Some suitable, but non-limiting, examples of materials for the cushioning members 324 and/or plurality of anchor members 344 are discussed below.

In some examples, the cushioning members 324 and the plurality of anchor members 344 may be integrally formed and/or cut from a unitary member. In some embodiments, the cushioning members 324 and the plurality of anchor members 344 may be integrally formed and/or cut from a unitary tubular member and subsequently formed and/or heat set to a desired shape in the expanded configuration. In some embodiments, the cushioning members 324 and the plurality of anchor members 344 may be integrally formed and/or cut from a unitary flat member, and then formed into a structure illustrated in FIG. 6. Some exemplary means and/or methods of making and/or forming the cushioning members 324 and the plurality of anchor members 344 include laser cutting, machining, punching, stamping, electro discharge machining (EDM), chemical dissolution, etc. Other means and/or methods are also contemplated.

As illustrated in FIG. 6, the plurality of anchor members 344 disposed along the cushioning members 324 may include two rows of anchor members 344. However, this is not intended to be limiting. Rather, the expandable framework 312 may include a single row of anchor members 344. In other examples, the expandable framework 312 may include more than two rows of anchor members 344. For example, in some instances the expandable framework 312 may include 1, 2, 3, 4 or more rows of anchor members 344.

Figure 7:
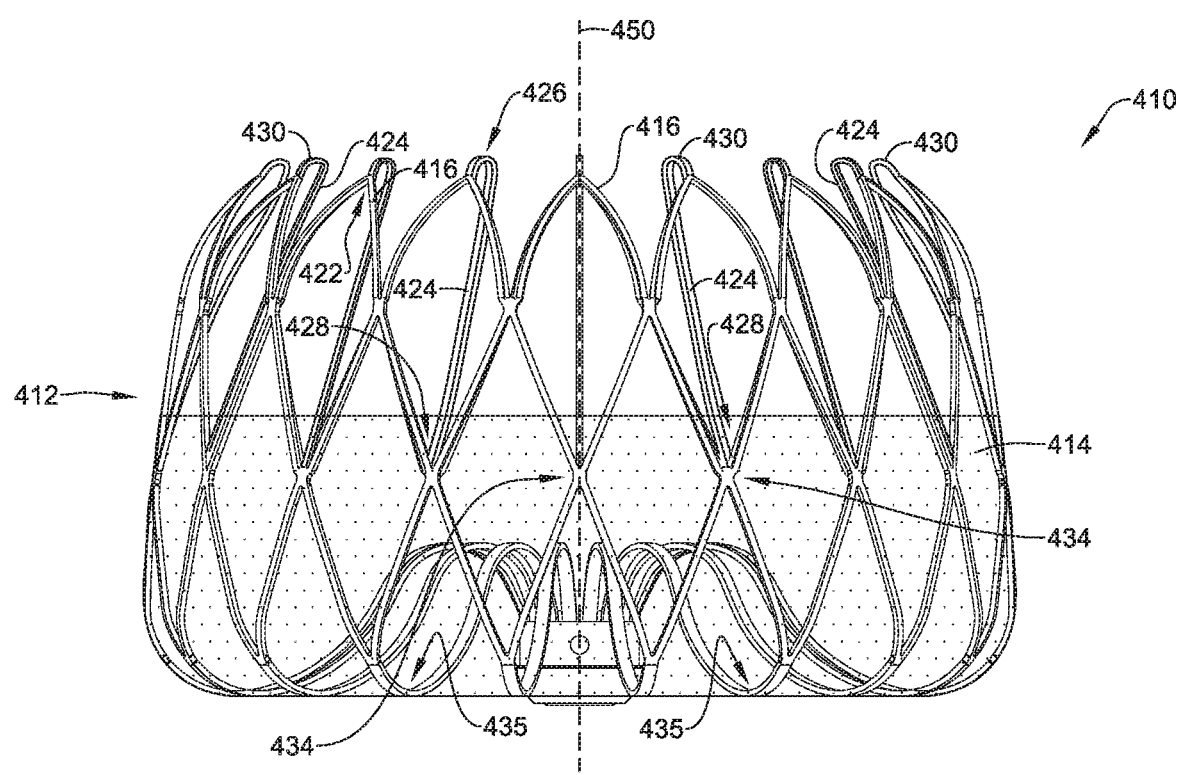
FIG. 7 illustrates another example occlusive implant.

FIG. 7 illustrates a detailed view of another example occlusion implant device 410. The occlusion implant device 410 may be similar in form and function to other occlusion implant devices disclosed herein. For example, the occlusion implant device 410 may include an occlusive member 414 and an expandable frame 412 including one or more cushioning members 424 extending from one or more corresponding projections 416. Further, each of the cushioning members 424 may include a first end region 426 attached to a corresponding projection 416 at an apex 422 and a second end region 428 attached to an inner surface 435 of the expandable framework 412 at an intersection 434 (e.g., the second end region 428 may attach to an opposite side of the intersection 34 described with respect to FIG. 2).

It can be appreciated that (in contrast to the occlusive implant 10 described with respect to FIG. 2), that the cushioning members 424 of FIG. 7 may bend inward toward a central axis 450 of the occlusive implant 410. Similar to the cushioning members 24 described with respect to FIG. 2, the cushioning members 424 may form a curved region 430 extending along a length thereof. Further, the curved portions 430 of the cushioning members 424 may function similarly to the curved portions 30 described with respect to FIG. 2.

Figure 8:
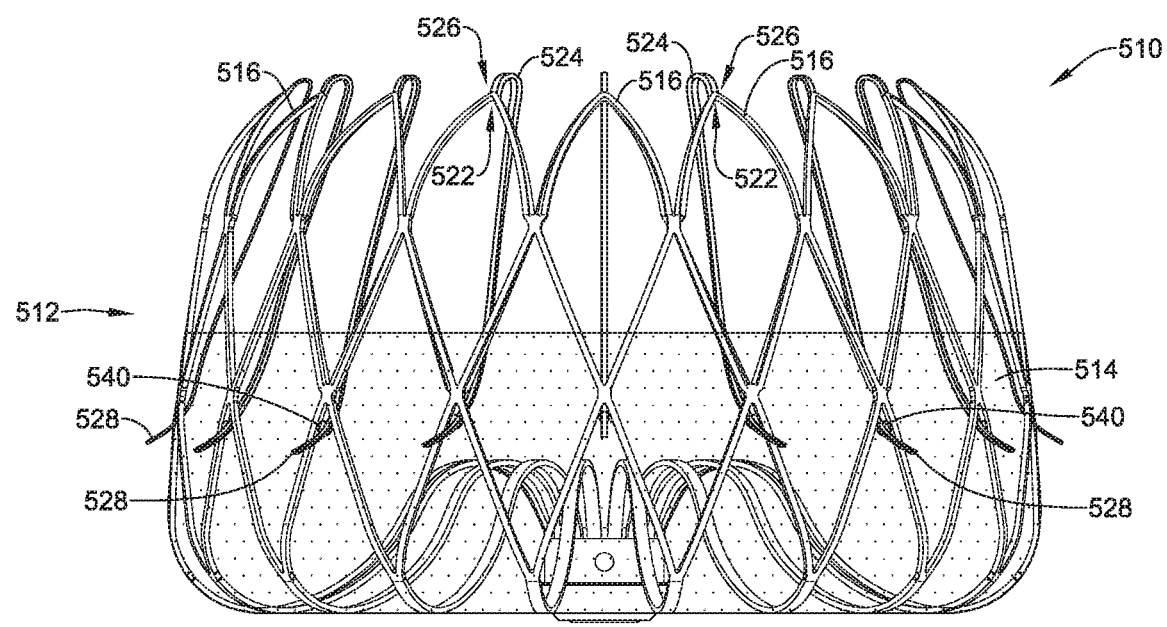
FIG. 8 illustrates another example occlusive implant.

FIG. 8 illustrates another example occlusion implant device 510. The occlusion implant device 510 may be similar in form and function to other occlusion implant devices disclosed herein. For example, the occlusion implant device 510 may include an occlusive member 514 and an expandable frame 512 including one or more cushioning members 524 extending from one or more corresponding projections 516. Further, each of the cushioning members 524 may include a first end region 526 attached to a corresponding projection 516 at an apex 522. Additionally, FIG. 8 illustrates that in some examples, the cushioning members 524 may include a second end region 528 which extends through an aperture 540 (shown in greater detail in FIG. 9) formed in the occlusive member 514.

Figure 9:
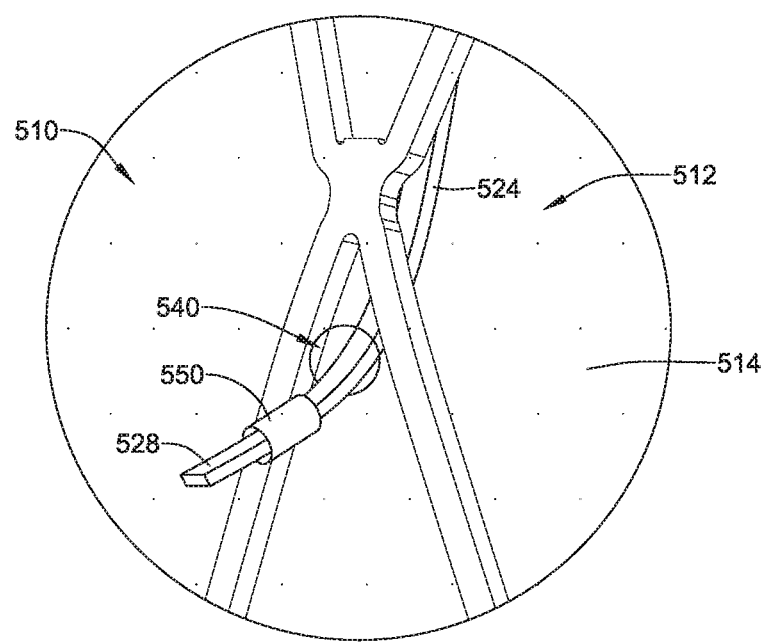
FIG. 9 illustrates another example occlusive implant.

FIG. 9 illustrates a detailed view of an attachment technique for attaching an example occlusive member 514 to an expandable framework 512 of an example occlusion device 510 (illustrated and described with respect to FIG. 8). FIG. 9 illustrates that in at least some examples, the occlusive member 514 may include an aperture 540 through which the second end region 528 of the cushioning member 524 may extend. It can be appreciated that the occlusive member 514 may be rigidly attached (e.g., glued, etc.) to the second end region 528 of the cushioning member 524. Additionally, while not shown in FIG. 9, it is contemplated that the cushioning member 524 may include one or more features which may prevent its detachment from the occlusive member 514. For example, the second end region 528 may include a barb-like feature designed to prevent the second end region 528 from detaching from occlusive member 514.

Similar to that discussed above with respect to FIG. 4, it is contemplated that the cushioning member 524 shown in FIG. 9 need not be attached to the expandable framework 112. For example, it is contemplated that the second end region 528 of the cushioning member 524 may "slide" or translate through the aperture 540. It can be appreciated that the length of the second end region 528 of the cushioning member 524 may be designed to prevent the second end region 528 from passing back through the aperture 540. Additionally, FIG. 9 illustrates that in some instances the second end region 528 may include a tubular component 550 which may be coupled to the second end region 528. The tubular component 550 may prevent the second end region 528 from sliding back through the aperture 540.

The materials that can be used for the various components of the occlusive implant 10 (and variations, systems or components thereof disclosed herein) and the various elements thereof disclosed herein may include those commonly associated with medical devices. For simplicity purposes, the following discussion makes reference to the occlusive implant 10 (and variations, systems or components disclosed herein). However, this is not intended to limit the devices and methods described herein, as the discussion may be applied to other elements, members, components, or devices disclosed herein.

In some embodiments, the occlusive implant 10 (and variations, systems or components thereof disclosed herein) may be made from a metal, metal alloy, polymer (some examples of which are disclosed below), a metal-polymer composite, ceramics, combinations thereof, and the like, or other suitable material. Some examples of suitable metals and metal alloys include stainless steel, such as 444V, 444L, and 314LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; platinum; palladium; gold; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the occlusive implant 10 (and variations, systems or components thereof disclosed herein) may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the occlusive implant 10 (and variations, systems or components thereof disclosed herein). Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the occlusive implant 10 (and variations, systems or components thereof disclosed herein). to achieve the same result.

In some embodiments, a degree of Magnetic Resonance Imaging (MRI) compatibility is imparted into the occlusive implant 10 (and variations, systems or components thereof disclosed herein). For example, the occlusive implant 10 (and variations, systems or components thereof disclosed herein) and/or components or portions thereof, may be made of a material that does not substantially distort the image and create substantial artifacts (e.g., gaps in the image). Certain ferromagnetic materials, for example, may not be suitable because they may create artifacts in an MRI image. The occlusive implant 10 (and variations, systems or components disclosed herein) or portions thereof, may also be made from a material that the MRI machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N® and the like), nitinol, and the like, and others.

In some embodiments, the occlusive implant 10 (and variations, systems or components thereof disclosed herein) and/or portions thereof, may be made from or include a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, polyurethane silicone copolymers (for example, ElastEon® from Aortech Biomaterials or ChronoSil® from AdvanSource Biomaterials), biocompatible polymers, other suitable materials, or mixtures, combinations, copolymers thereof, polymer/metal composites, and the like. In some embodiments, the sheath can be blended with a liquid crystal polymer (LCP). For example, the mixture can contain up to about 6 percent LCP.

In some embodiments, the occlusive implant 10 (and variations, systems or components thereof disclosed herein) may include a textile material. Some examples of suitable textile materials may include synthetic yarns that may be flat, shaped, twisted, textured, pre-shrunk or un-shrunk. Synthetic biocompatible yarns suitable for use in the present disclosure include, but are not limited to, polyesters, including polyethylene terephthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum or a Ni—Co—Cr-based alloy. The yarns may further include carbon, glass or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun-types. The type and denier of the yarn chosen may be selected in a manner which forms a biocompatible and implantable prosthesis and, more particularly, a vascular structure having desirable properties.

In some embodiments, the occlusive implant 10 (and variations, systems or components thereof disclosed herein) may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethylketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); anti-neoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vascoactive mechanisms.

While the discussion above is generally directed toward an occlusive implant for use in the left atrial appendage of the heart, the aforementioned features may also be useful in other types of medical implants where a fabric or membrane is attached to a frame or support structure including, but not limited to, implants for the treatment of aneurysms (e.g., abdominal aortic aneurysms, thoracic aortic aneurysms, etc.), replacement valve implants (e.g., replacement heart valve implants, replacement aortic valve implants, replacement mitral valve implants, replacement vascular valve implants, etc.), and/or other types of occlusive devices (e.g., atrial septal occluders, cerebral aneurysm occluders, peripheral artery occluders, etc.). Other useful applications of the disclosed features are also contemplated.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. An occlusive implant, comprising:
   an expandable framework including a projection; and
   a cushioning member coupled to the expandable framework, the cushioning member including a first end region and a second end region opposite the first end region,
   wherein the cushioning member folds back on itself in a radial direction;
   wherein the first end region is coupled to an apex of the projection;
   wherein the second end region is coupled to the expandable framework;
   wherein the cushioning member includes a curved portion designed to minimize trauma to a target site;
   wherein the cushioning member extends longitudinally over an entirety of the projection.

2. The occlusive implant of claim 1, wherein the second end region of the cushioning member is attached to an outer surface of the expandable framework.

3. The occlusive implant of claim 1, wherein the second end region of the cushioning member extends through an aperture formed in the expandable framework.

4. The occlusive implant of claim 3, wherein the cushioning member is configured to translate through the aperture formed in the expandable framework.

5. The occlusive implant of claim 1, further comprising an occlusive member disposed along at least a portion of the expandable framework.

6. The occlusive implant of claim 5, wherein the occlusive member is attached to the cushioning member.

7. The occlusive implant of claim 1, further comprising a plurality of projections extending circumferentially around a central axis of the expandable framework.

8. The occlusive implant of claim 7, further comprising a plurality of cushioning members, wherein each of the plurality of cushioning members is coupled to a corresponding projection.

9. The occlusive implant of claim 1, wherein the expandable framework is configured to shift between a collapsed configuration and an expanded configuration.

10. The occlusive implant of claim 1, wherein the cushioning member folds inward toward a central axis of the expandable framework.

11. The occlusive implant of claim 1, wherein the first end region and second end region of the cushioning member are longitudinally aligned.

* * * * *